(12) United States Patent
Sidebotham et al.

(10) Patent No.: US 8,556,897 B2
(45) Date of Patent: Oct. 15, 2013

(54) MODULAR SPHERICAL HOLLOW REAMER ASSEMBLY FOR MEDICAL APPLICATIONS

(76) Inventors: Christopher G. Sidebotham, Mendham, NJ (US); Randall J. Lewis, Bethesda, MD (US)

( * ) Notice: Subject to any disclaimer, the term of this patent is extended or adjusted under 35 U.S.C. 154(b) by 0 days.

(21) Appl. No.: 12/072,671

(22) Filed: Feb. 27, 2008

(65) Prior Publication Data

US 2008/0195106 A1    Aug. 14, 2008

Related U.S. Application Data

(63) Continuation-in-part of application No. 11/973,260, filed on Oct. 5, 2007, which is a continuation-in-part of application No. 11/704,754, filed on Feb. 9, 2007.

(51) Int. Cl.
*A61B 17/00* (2006.01)

(52) U.S. Cl.
USPC .............................................. 606/81

(58) Field of Classification Search
USPC .................. 606/79–81, 89, 91, 86 R, 102; 623/22.31–22.32, 22.21, 22.27, 623/22.11–22.12, 22.25
See application file for complete search history.

(56) References Cited

U.S. PATENT DOCUMENTS

| | | | | |
|---|---|---|---|---|
| 4,023,572 A | * | 5/1977 | Weigand et al. | 606/81 |
| 4,116,200 A | | 9/1978 | Braun et al. | 605/81 |
| 4,811,632 A | | 3/1989 | Salyer | 76/115 |
| 5,100,267 A | * | 3/1992 | Salyer | 407/54 |
| 5,116,165 A | | 5/1992 | Salyer | 407/54 |
| 5,171,312 A | | 12/1992 | Salyer | 606/81 |
| 5,171,313 A | | 12/1992 | Salyer | 606/86 |
| 5,190,548 A | * | 3/1993 | Davis | 606/80 |
| 5,236,433 A | | 8/1993 | Salyer | 606/91 |
| 5,282,804 A | | 2/1994 | Salyer | 606/86 |
| 5,299,893 A | | 4/1994 | Salyer | 407/54 |
| 5,364,403 A | * | 11/1994 | Petersen et al. | 606/91 |
| 5,376,092 A | * | 12/1994 | Hein et al. | 606/81 |
| 5,431,657 A | * | 7/1995 | Rohr | 606/91 |
| 5,462,548 A | * | 10/1995 | Pappas et al. | 606/80 |

(Continued)

FOREIGN PATENT DOCUMENTS

WO    WO/9007908    7/1990

OTHER PUBLICATIONS

"Single Use Sterile Power Equipment", Orthomedix.com, at http://www.orthomedex.com/index.html.

(Continued)

*Primary Examiner* — Matthew Lawson
(74) *Attorney, Agent, or Firm* — Ernest D. Buff; Ernest D. Buff & Assoc. LLC; Dave Narasimhan

(57) ABSTRACT

An easy-to-assemble, disposable spherical hollow reamer for medical applications includes a shaft portion, a disposable spherical hollow reamer and a central conical plate. The shaft portion has a proximal end for attachment to a drill, a central conical element and a distal precision threaded screw end. The spherical hollow reamer has plurality of cutters and apertures that extend through its thickness. The spherical hollow reamer has a precision threaded aperture that engages with the threaded end of the reusable shaft precisely aligning the centerline of the shaft with that of the spherical hollow reamer, providing wobble free reaming action. The central conical plate in combination with the interior surface of the spherical hollow reamer forms an enclosed space for capturing bone fragment and bone cement debris.

8 Claims, 8 Drawing Sheets

(56) References Cited

U.S. PATENT DOCUMENTS

| | | | |
|---|---|---|---|
| 5,501,686 A | 3/1996 | Salyer | 696/79 |
| 5,540,697 A * | 7/1996 | Rehmann et al. | 606/91 |
| 5,549,613 A | 8/1996 | Goble et al. | 606/80 |
| 5,556,399 A | 9/1996 | Huebner | 606/80 |
| 5,584,837 A * | 12/1996 | Petersen | 606/91 |
| 5,690,634 A | 11/1997 | Muller et al. | 606/80 |
| 5,709,688 A | 1/1998 | Salyer | 606/81 |
| 5,755,719 A | 5/1998 | Frieze | 606/81 |
| 5,817,096 A * | 10/1998 | Salyer | 606/81 |
| 5,879,355 A * | 3/1999 | Ullmark | 606/93 |
| 5,897,355 A * | 4/1999 | Bulucea et al. | 438/273 |
| 5,908,423 A | 6/1999 | Kashuba et al. | 606/80 |
| 5,919,195 A * | 7/1999 | Wilson et al. | 606/80 |
| 5,954,671 A | 9/1999 | O'Neill | 600/567 |
| 5,976,144 A | 11/1999 | Fishbein et al. | 606/80 |
| 5,976,148 A * | 11/1999 | Charpenet et al. | 606/91 |
| 5,980,170 A | 11/1999 | Salyer | 408/239 R |
| 6,001,105 A | 12/1999 | Salyer | 606/81 |
| 6,162,226 A * | 12/2000 | DeCarlo et al. | 606/80 |
| 6,168,600 B1 * | 1/2001 | Grace et al. | 606/81 |
| 6,193,722 B1 | 2/2001 | Zech et al. | 606/79 |
| 6,198,914 B1 * | 3/2001 | Saegusa | 455/404.2 |
| 6,250,858 B1 * | 6/2001 | Salyer | 408/239 R |
| 6,283,971 B1 | 9/2001 | Temeles | 606/81 |
| 6,332,886 B1 | 12/2001 | Green et al. | 606/80 |
| 6,383,188 B2 | 5/2002 | Kuslich et al. | 606/80 |
| 6,409,732 B1 | 6/2002 | Salyer | 606/91 |
| 6,428,543 B1 | 8/2002 | Salyer | 606/81 |
| 6,451,023 B1 | 9/2002 | Salazar et al. | 606/86 |
| 6,730,094 B2 | 5/2004 | Salyer et al. | 606/80 |
| 6,854,742 B2 | 2/2005 | Salyer | 279/93 |
| 6,875,217 B2 | 4/2005 | Wolford | 606/81 |
| 6,951,563 B2 * | 10/2005 | Wolford | 606/81 |
| 7,074,224 B2 * | 7/2006 | Daniels et al. | 606/80 |
| 7,090,678 B2 * | 8/2006 | Cotting et al. | 606/81 |
| 7,118,575 B2 * | 10/2006 | Wolford | 606/80 |
| 7,217,272 B2 * | 5/2007 | Salyer | 606/80 |
| 7,220,264 B1 * | 5/2007 | Hershberger | 606/81 |
| 7,621,921 B2 * | 11/2009 | Parker | 606/91 |
| 7,632,276 B2 * | 12/2009 | Fishbein | 606/80 |
| 2003/0181916 A1 | 9/2003 | Wolfdord | 606/81 |
| 2004/0073224 A1 * | 4/2004 | Bauer | 606/81 |
| 2004/0073226 A1 * | 4/2004 | Cotting et al. | 606/91 |
| 2005/0049601 A1 * | 3/2005 | Keller | 606/81 |
| 2005/0085823 A1 * | 4/2005 | Murphy | 606/91 |
| 2005/0113836 A1 | 5/2005 | Lozier et al. | 606/80 |
| 2006/0004371 A1 | 1/2006 | Williams et al. | 606/80 |
| 2006/0095041 A1 | 5/2006 | Fehlbaum et al. | 606/81 |
| 2006/0106393 A1 * | 5/2006 | Huebner et al. | 606/80 |
| 2006/0184174 A1 | 8/2006 | Harris et al. | 606/80 |
| 2006/0235539 A1 | 10/2006 | Blunn et al. | 623/22.12 |
| 2006/0241629 A1 | 10/2006 | Krebs et al. | 606/80 |
| 2006/0264956 A1 | 11/2006 | Orbay et al. | 606/80 |
| 2007/0233132 A1 * | 10/2007 | Valla | 606/81 |

OTHER PUBLICATIONS

"Effect of Flexible Drive Diameter and Reamer Design on the Increase of Pressure in the Medullary Cavity During reaming", Mueller et al., PubMed (1993) http://www.ncbi.nlm.nih.gov/entrez/query.fcgi?db=pubmed&cmd=Retrieve&dopt=AbstractPlus&list_uids=8168875&query_hl=2&itool=pubmed_Brief.

* cited by examiner

MODULAR SPHERICAL HOLLOW REAMER ASSEMBLY FOR MEDICAL APPLICATIONS

This is a Continuation-In-Part of application Ser. No. 11/973,260, filed Oct. 5, 2007 for "Modular Tapered Hollow Reamer For Medical Applications" which, in turn, is a Continuation-In-Part of application Ser. No. 11/704,754, filed Feb. 9, 2007, the disclosures of which are hereby incorporated in their entirety by reference thereto.

BACKGROUND OF THE INVENTION

1. Field of the Invention

The present invention relates to a modular easy-to-assemble modular spherical hollow reamer assembly for medical applications; and more particularly, to a spherical hollow reamer having a disposable spherical reamer, which can be attached concentric to the centerline of a reusable shaft portion and includes a bone fragment and bone debris capturing cavity.

2. Description of the Prior Art

Reaming of the internal canal of bones is required in many surgical procedures of orthopedic surgery. These procedures include hip replacement and shoulder replacement, and the like. Reamers are used in procedures that involve creation of acetabular bone cavities that accept a properly sized acetabular cups. Prior art reamers typically fall into two major classes: rigid and flexible shaft. Typically, reaming of the internal bone cavity is achieved through utilization of a solid spherical reamer some having provisions for discharging and collecting reamed bone fragments. Solid spherical reamers currently utilized are required to cut both cancellous bone (spongy bone) and cortical bone (hard bone). Cortical bone is generally denser and stronger, requiring an efficient cutter to machine the acetabular cavity for a proper fit of the acetabular cup. Conventional spherical reamers can cut cortical bone initially but can quickly dull after a single use, or at best a few uses. Once the reamer has dull cutting edges, it reduces the efficiency of bone cutting and in addition generates sufficient friction/heat to damage or kill the surrounding bone. These prior art solid spherical reamers are intended for multiple uses and therefore become less efficient after each surgery, resulting in poor cutting performance and bone necrosis. These dull blades also incorporate bone debris or bone cement debris into the living bone tissue, creating bone healing problems and fixation of an implanted acetabular cup.

U.S. Pat. No. 4,116,200 to Braun et al. discloses a milling tool for surgical purposes. This surgical milling tool is operated with a hand-operated milling machine for milling the heads or sockets of bone joints of a spherical shape. The tool is formed of a hemispherical cup integrally formed with a cylindrical skirt and flange and is provided with a plurality of openings of semi-oval shape, each having a cutting edge arranged at the minor axis of the oval shape. The openings are situated such that, upon rotation of the cup, the cutting edges thereof overlap to provide a continuous cutting edge surface conforming generally to the shape of the cup. The formation of fine bone shavings is avoided by use of this milling tool. The surgical milling tool utilizes a integrally formed hemispherical cup having a plurality of openings appointed with cutting edges for milling sockets of bone joints. The hemispherical shape of cup provides the ability to hollow out the arcuate shape of the bone joints. Bone and cartilage shavings are formed during the milling process and are collected in a border area inside of the hemispherical cup. The surgical milling tool is provided for multiple use and is not a disposable spherical hollow reamer, and therefore the tool will become less efficient after each surgery, resulting in poor cutting performance and bone necrosis.

U.S. Pat. No. 4,811,632 to Salyer discloses surgical reamer. a method of producing an acetabular reamer cup. This method comprises the steps of fabricating a bowl-shaped cup-blank having an outer surface, an inner surface and a rim, perforating a plurality of holes through the cup-blank, the holes each being surrounded by a margin, deforming outwardly a cutting portion of the margin of each of the holes, smoothing the outer surface of the cup-blank to sharpen the deformed cutting portions, raising cutting edges from the cutting portions and removing the rim. The cutting edges are disposed to cut upon rotation of the acetabular reamer. The cup manufactured by this method is preferred because of its improved strength and consistently superior cutting edges. The acetabular reamer utilizes a hemispherical or bowl-shaped cup having a spherical construction and a plurality cutting openings for milling sockets of joints. The hemispherical shape of reamer provides the ability to hollow out the arcuate shape of the bone joints. The acetabular reamer is provided for multiple use, and therefore the tool will become less efficient after each surgery, resulting in poor cutting performance and bone necrosis.

U.S. Pat. No. 5,100,267 and its continuation in part U.S. Pat. No. 5,299,893 to Salyer disclose a disposable acetabular reamer cup. The disposable acetabular reamer cup has a cutting bowl having a plurality of cutting edges. The cutting bowl has perforations adjoining the cutting edges. The cutting bowl defines an axis of rotation. The cutting bowl has a bottom opening. A transparent polymeric plug is joined to the cutting bowl. The plug is concentric with the axis of rotation. It occupies the bottom opening; and has a tool driver opening concentric with the axis of rotation. When a torque is applied, the bowl is turned with respect to the plug, which means that the cutting torque is transmitted through the plug and transferred to the cutting plug through the detents. There is no direct connection between the shaft and the cutting bowl other than through the plug. Concentricity of the cutting bowl with respect to that of the shaft is therefore not assured.

U.S. Pat. No. 5,116,165 to Salyer discloses an acetabular reamer cup. This acetabular reamer cup comprises a cutting bowl having a plurality of singly curved cutting edges. The cutting bowl has a plurality of slots preceding the cutting edges. The cutting bowl defines an axis of rotation. A bottom is joined to the cutting bowl. The bottom has a tool driver opening concentric with the axis of rotation. With a right handed acetabular reamer cup that cuts when pressed against a substrate and rotated in a clockwise direction, slots are positioned to the right of respective cutters. There is no direct connection between the shaft and the cutting bowl other than through the base aperture. The concentricity of the cutting bowl with respect to that of the shaft is therefore not assured.

U.S. Pat. No. 5,376,092 to Hein, et al. discloses a reamer for shaping bone sockets. This reamer shapes a socket, such as a hip socket. It comprises a cutting head located at one end of a rotatably driven shaft and having a hemispherical portion with a hemispherical exterior surface. The hemispherical portion contains an open substantially hollow chamber and helical openings such as slots, in said hemispherical portion connecting between the exterior surface and the chamber. The trailing portion of each of the openings has a cutting or trailing edge raised slightly above the leading edge of the opening or slot to move material from the socket into the chamber during rotation of the cutting head. The cutting edges having serrations thereon. At least two cutting edges extending across the polar region of the cutting head. A stem extending from the interior center point of the substantially hollow chamber and extending along the polar axis of the hemispherical reamer for connecting and disconnecting the cutting head to a rotatable source. The reamer for shaping bones is a solid reamer that is not disposable. It is attached to a drive shaft by sliding the shaft into an aperture and locking with a pin, as shown in the drawing. Since there is always a slack between a cylindrical shaft and a cylindrical aperture, the reamer is not centered in alignment with the shaft centerline.

U.S. Pat. No. 5,709,688, as well as U.S. Pat. Nos. 6,001,105, and 6,428,543 to Salyer disclose an acetabular reamer cup and method of producing the same. This method for making an acetabular reamer cup for an acetabular reamer comprises the steps of: fabricating a bowl shaped cup-blank having outer and inner bowl shaped surfaces, perforating a plurality of holes through the cup-blank, the holes each are surrounded by a curved margin, deforming outwardly of the outer surface a cutting portion of the margin of each of the holes, thereby forming cutting edges, the cutting portions are curved outwardly of the outer surface, the cutting edges are curved tangentially of the outer surface and disposed to cut upon rotation of the acetabular reamer. An acetabular reamer cup is also provided with a cutting bowl having a plurality of curved cutting edges. The cutting bowl has a plurality of openings preceding the cutting edges, and a generally conical rise following the cutting edges. The cutting edges are spirally arranged about the axis of rotation of the cutting bowl, and a bottom adjoined to the cutting bowl. The bottom has a tool driver opening coaxial with the cutting bowl and the cutting edges. Bone debris collection compartment is located directly below the acetabular reamer. Bottom of the acetabular reamer has a tool driver opening, which is concentric with the cutting bowl. The driver opening engages with the shaft, which drives the acetabular reamer. This form of attachment of the shaft with the acetabular reamer does not ensure alignment of axis of the shaft with that of the acetabular reamer. The acetabular reamer is not indicated to be disposable.

U.S. Pat. No. 5,755,719 to Frieze, et al. discloses an acetabular reamer. This acetabular reamer includes a base, a first set of semi-circular blades attached to the base, and a second set of semi-circular blades also contacting said base, and crossing and intersecting with said first set of blades at right angles thereto. The base preferably comprises a circular plate having a hexagonal drive hole in the center thereof and a plurality of slots in the periphery thereof for anchoring the blades. Each semi-circular blade includes a first end having a projection thereon, a second end opposite from said first end and also having a projection thereon, a first edge having serrated cutting teeth thereon, a second edge opposite from said first edge, and a first and second side surface. The cutting edge of the first set of blades includes a plurality of outwardly facing slots, which mate with and engage a second set of inwardly facing slots in the second edge of said second blades. When the first and second set of blades are assembled in this fashion the cutting edges of both sets of blades lie in the same spherical plane. The projections can comprise snap-in projections that automatically lock in position or projections that can be twisted and locked into position. Alternatively, the base can comprise a pair of upper and lower plates with apertures in the upper plate such that when the blade projections mate with the apertures, riveting of the lower plate with respect to the upper plate locks the projections and their related blades into position on the base. When the reamer is assembled it has a hemispherical shape suitable for reaming the acetabulum of the hip so that the acetabular portion of a hip implant properly fits into the acetabulum. The acetabular reamer is an open structure and the bone fragments will migrate back into the cutting zone, since no containment space is formed by the open structure of the cutter blades inserted into the base. The drive shaft is coupled to a hexagonal aperture in the base plate and this method of attachment does not align the hemispherical cutter centerline with that of the drive shaft resulting in the wobbliness of the cutter in the bone cavity.

U.S. Pat. No. 5,976,144 to Fishbein et al. discloses a hollow dome reamer with removable teeth. This surgical reamer has a hollow dome with apertures spaced apart arranged in arcs extending from an apex of the dome to the base portion of the dome. Removable teeth are positioned in the apertures. Each cutting tooth has a flange that is aligned flush with the external surface of the dome, and a raised cutting edge extending above the flange and the external surface of the dome. An interior passageway communicates between the outside and inside of the dome. A base plate is removably secured on the base portion of the dome to provide closure of the central cavity of the dome. A perspective view of the cutter of the reamer is shown hereinbelow on the left; a perspective view of the reamer with removable, replaceable cutters is shown herein on the right. The base plate is secured to the dome by retaining springs. A drive shaft is connected to the base plate through an aperture in the base plate and held in place by a spring. The surgical reamer has a hollow dome with apertures spaced apart appointed to receive removable teeth positioned therein. Although the teeth are removable, they are not disposable in nature; the teeth are removed for replacement or for re-sharpening and are used again. The dome is connected to a base plate, which is further connected to a shaft member and retained by a spring clip and an interlocking latch. There is no direct attachment of the shaft to the dome and this multitude of connections to the shaft does not assure that the centerline of the shaft coincides with that of the hollow dome.

U.S. Pat. No. 5,980,170 to Salyer as well as U.S. Pat. Nos. 5,817,096, 5,501,686, 5,282,804, 5,236,433, 5,171,313, 5,171,312 disclose a tool driver. This tool driver has a shaft with a longitudinal axis and opposite ends. A boss is secured at one of said shaft ends by which the tool driver is connected to a rotary tool. A tool collate is secured at the other of the shaft ends by which the tool driver may be driven by a surgical hand piece having a chuck in which the collate may be positioned. The boss has a distal end surface with a groove therein. Both the groove and the distal end surface extend transversely of the axis. A pin is positioned in the groove on the axis. A latch mechanism is provided to hold a mounting bar of a rotary tool in the groove on the pin, whereby the rotary tool is held exactly coaxially of the driver during use. The rotary tool, which is used with the driver has a bar which has the same dimensions as the groove in the boss of the tool driver of the invention. The bar thus fills the slot and is complementary to the slot. The bar has a hole therein which is complementary to the pin. The pin extends coaxially of the shaft and the boss. The bar hole in which the pin of the tool driver is positioned is precisely coaxial of the axis of the tool about which the cutting edges are precisely positioned. The tool driver has a shaft appointed to receive acetabular reamer cups and patella cutters. The cutters are appointed to be connected to the tip of the shaft by means of mounting bar in the cutter and a slot in the shaft secured by a complementary pin. This method of attachment using a mounting bar that slides into a slot clearly does not align the centerline of the shaft and that of the reamer.

U.S. Pat. No. 6,168,600 to Grace, et al discloses an acetabular reamer backing plate and method of use. This backing plate is for an acetabular reamer assembly that allows for the attachment of a reamer driver. The acetabular reamer assembly comprises a cutting cup and backing plate, the cutting cup having an external surface with cutting teeth formed therein and having an internal surface, the cutting cup terminating in a peripheral edge. The rigid backing plate has a planar surface, which terminates in an outer circumferential edge, the outer circumferential edge being coupled to the peripheral bottom edge of the cutting cup, the rigid plate also having an internal edge profile. The internal edge profile of the rigid backing plate has at least two finger elements protruding from the outer circumferential edge thereof towards a central vertical axis drawn perpendicular to the planar surface of the plate. Further, the finger elements of the backing plate form a holding opening for a reamer driver. The internal edge profile of the backing plate forms at least one observation opening in addition to the holding opening to allow bone fragments forming within the acetabular reamer to be visually inspected while the reamer is in use. The finger elements terminate to form a contact surface to make firm contact with the driver when inserted in the holding opening. The contact surface can be simple or complex. Further, the internal edge profile is continuous so that the machining process for the backing plate is simplified. The acetabular backing plate is welded or mechanically attached to the spherical reamer and the shaft is connected to the backing plate via a slidable attachment. Due to the clearance at the sliding interface, the centerline of the spherical reamer need not coincide with that of the drive shaft and the cutting action can be wobbly. The welded spherical reamer is not indicated to be a disposable spherical hollow reamer.

U.S. Pat. No. 6,409,732 to Salyer discloses a tool driver. This tool driver has a shaft with a longitudinal axis and opposite ends. A boss is secured at one of the shaft ends by which the tool driver is connected to a rotary tool. A tool collate is secured to the other of the shaft ends by which the tool driver may be driven by a surgical hand piece having a chuck in which the collate may be positioned. The boss is equipped with a securing device of the bayonet type having a latch mechanism, which holds the rotary tool on the boss coaxially of the driver during use. The securing device has a tapered bore extending from the distal end of the boss axially of the shaft. The rotary tool has a diametrical bar extending across a bottom tool driver opening with a centrally located circular disk therein. The disk of the rotary tool fits within the bore of the tool shaft boss so as to concentrically locate the rotary tool and the tool shaft on the same axis. The latch mechanism holds the tool driver and the tool together in this position, whereby rotary tools of a multitude of sizes can be secured concentrically to the tool shaft without holding a plurality of critical tolerances when machining the bayonet type securing device or the rotary tool bottom bar. The tool driver is a shaft with a slot on the end that receives the acetabular reamer. It deals with the details of the device for attaching the acetabular reamer to the shaft. This type of slotted attachment does not result in coaxial mounting of the reamer that is coincident with the centerline of the shaft, even though the different components of the shaft are said to be coaxially aligned. The reamer is not indicated to be disposable.

U.S. Pat. No. 6,730,094 to Salyer et al. discloses cutting edges for reamers and a method for making same. Each reamer has a plurality of cutters spirally arranged on reamer surface. Each cutter has a continuous cutting edge. Edges may be generally straight in planes perpendicular to the reamer surface or tangential or parallel to the tangential plane with respect to the reamer surface. Cutting edges may also be curved in planes perpendicular to the reamer surface or parallel or tangential to the reamer surface. Further, the curvature may be convex, or concave or of other complex shapes. There need be no relationship between the shape of cutting edges and the shape of reamer surface. In fact, one may be curved and the other straight, or both may be curved in the same or opposite directions. These relate to the edge geometry of the cutting edges of the reamer. As explicitly stated in the summary, "It is also an advantage of the invention to provide a new and improved reamer that can be stripped in the field and sterilized for re-use, and which does not have crevices and other structures to hold bone chips and tissue which cannot be easily dislodged prior to sterilization", the reamer is intended to be reused after sterilization and is not a disposable spherical reamer.

U.S. Pat. No. 6,875,217 to Wolford discloses an orthopedic reamer assembly. This orthopedic reamer assembly includes a reamer with a generally hemispherical shell having a concave side and at least one attachment feature associated with the concave side. A driver is attachable to the reamer and has a shaft with a reamer end. A releasable collar is disposed on the reamer end, which includes a boss having at least one retaining pin. A sleeve is fitted over the boss and includes a groove that is proximate to a corresponding retaining pin. The reamer has a cavity in the reamer end with a biasing element. The biasing element biases the sleeve in a closed position respective to the boss. A release pin, which press fits into the sleeve is provided in the reamer end, and is conveyed through the cavity, with the biasing element biasing against the release pin. The orthopedic reamer assembly is a complicated attachment of design of the drive shaft to an acetabular reamer with multiple sliding parts. Since each of the sliding parts requires a sliding fit, there are inherent displacement possibilities and therefore, the centerline of the shaft is not reliably aligned with the centerline of the acetabular reamer. Moreover, the acetabular reamer is not indicated to be a disposable spherical hollow reamer and has complicated machined elements for sliding fit.

U.S. Patent Application Publication No. 2003/0181916 to Wolford discloses an orthopedic reamer with flat cutting teeth. This orthopedic reamer is for cutting bone and includes a shaft and a head coupled with the shaft. The head includes a distal face with a plurality of cutting teeth. Each cutting tooth includes a hole extending through the head. At least a portion of each hole has a substantially round perimeter. A raised lip is positioned adjacent to and extends around at least part of the substantially round portion. The '916 publication discloses an orthopedic reamer with flat cutting teeth having a shaft attached to acetabular reamer cups. The reamer cups of the '916 publication are not disposable in nature. The orthopedic reamer with flat cutting teeth publication does not provide a spherical hollow reamer assembly including a space for capturing bone fragments or bone cement debris. The attachment of the acetabular reamer to the drive shaft includes a complicated mechanism and does not reliably align the centerline of the drive shaft with that of the acetabular reamer and therefore wobble free rotation is not provided.

U.S. Patent Application Publication No. 2006/0095041 to Fehlbaum et al. discloses contoured reamer teeth and method for their manufacture. An acetabular reamer has a cutting shell having a series of doubly curved cutting teeth of a quantity to substantially reduce a cutting pressure on each tooth as well as to reduce a size of a typical chip generated upon cutting. Substantially all the teeth each have a matched arc cutting edge of substantial length that has a cutting profile which substantially matches a profile of a shape to be cut. The apertures in which the cutting edges are formed have at least one flat edge by which a punch, used in the process of forming the edge may be oriented. Such a configuration reduces the number of teeth required to cut the shape. The contoured reamer teeth publication does not provide a reaming assembly. In addition, the contoured reamer teeth are not disposable in nature, and therefore over time will become dulled, thereby causing enhanced friction during reaming and potentially damaging the bone.

U.S. Patent Application Publication No. 006/0235539 to Blunn et al. discloses a surgical kit for hemiarthroplasty hip replacement. This kit comprises a femoral head and reamer. The kit is suited for performing a hip hemiarthroplasty, in which a femoral head is fitted directly into a socket reamed into the acetabular without any permanent liner or prosthetic acetabular being implanted. The reamer is used to ream out the acetabulum until cancellous bone is exposed so that it bleeds liquid containing stem cells. By selecting the size of the femoral head in accordance with the characteristics of the patient, the pressure imposed on the liquid/synovial fluid of the joint is in the range between 0.5 and 2 MPa This causes the stem cells to produce new cartilage between the bone and femoral head. The surgical kit for hip replacement utilizes a spherical head with elements for reaming a socket in an acetabulum. The spherical shape of reamer provides the ability to hollow out the arcuate shape of the bone joints. The surgical kit disclosed by the '539 publication is provided for multiple use, and therefore the tool will become less efficient after each surgery, resulting in poor cutting performance and bone necrosis. Significantly, the '539 publication does not teach a disposable spherical hollow surgical reamer tool that is attached to a drive shaft with coincident centerlines.

Foreign Publication No. WO 9007908 to Schelhas discloses an acetabulum reamer. Acetabulum reamer for reaming the acetabulum of the human pelvic bone prior to insertion of an artificial hip joint cup comprises a reamer head on a shaft and a spiral reaming ridge arranged about the axis of the shaft and provided with reaming devices. The outer edge of the reaming ridge is delimited by a section of a spherical surface whose axis of rotation is flush with the axis of the shaft. The acetabulum reamer utilizes a spherical head for reaming a socket in an acetabulum. The spherical shape of reamer provides the ability to hollow out the arcuate shape of the bone joints. The reamer is provided for multiple use, and therefore the tool will become less efficient after each surgery, resulting in poor cutting performance and bone necrosis. Significantly, the acetabulum reamer publication does not teach a disposable spherical hollow surgical reamer tool that is attached to a drive shaft with coincident centerlines.

There remains a need in the art for a modular easy-to-assemble spherical hollow reamer for medical applications having a disposable spherical hollow cutter. Also needed in the art is a disposable spherical hollow cutter assembly of the type described, which can be attached concentric to a reusable shaft portion that provides means for reaming of an acetabular bone cavity in bones without any wobbly movement. Further needed in the art is a cutter assembly having means for collecting bone debris and keeping the collected debris displaced from the cutting portion, so that heat generated at the bone cutting surface is minimized. After one use of the spherical hollow reamer a new spherical hollow cutter with sharp fresh cutting edges can be utilized and the old hollow cutter can be discarded.

SUMMARY OF THE INVENTION

The present invention provides a modular easy-to-assemble spherical hollow reamer for medical applications having a disposable spherical reamer concentrically attached to a reusable shaft portion. The attachment between the disposable spherical hollow reamer and the reusable shaft is accomplished by a precision threaded screw attachment. The disposable spherical hollow reamer has in its interior a central precision machined screw member which threads directly into a threaded aperture at the distal end of the reusable shaft. These threads typically have 40 threads per inch, preferably ACME threads similar to that present in a precision micrometer. Since these threads are formed during the machining of the shaft and machining of the spherical hollow reamer, their centerlines are precisely aligned when the spherical hollow reamer is threaded into the distal end of the reusable shaft. Thus, when the proximal end of the reusable shaft is inserted into a drilling machine and the shaft is rotated, the disposable spherical hollow reamer rotates without any wobbliness and reams or cuts a precise bone cavity replicating the shape of the spherical hollow reamer.

Cutting teeth and bone fragment discharging apertures are provided on the outer surface of the spherical hollow cutter. The reusable shaft has an integral or user-attachable plate that encloses a volume within the spherical hollow reamer. In combination, the plate and reusable shaft provide a space for accumulation of bone debris or bone cement debris. The quick removal of bone fragments or bone cement debris reduces the amount of heat generated during the cutting/reaming procedure. Graduations are provided in the reusable shaft portion to determine the depth of insertion of the spherical hollow reamer into the bone cavity.

Generally stated, the Hollow Spherical Reamer for Medical Applications broadly comprises: (i) a reusable shaft portion having a threaded distal end, a proximal end for coupling with a drilling machine and a central region for a plate; (ii) a disposable spherical reamer portion with a plurality of cutting teeth and apertures for discharging bone and bone cement fragments; (iii) said disposable hollow reamer having a precisely machined screw element at the interior central location for attachment of the hollow spherical reamer to the reusable shaft distal end; (iv) said central region of the reusable shaft having a user attachable or integrally attached plate for creating a space within the hollow spherical reamer for collecting bone debris or bone cement debris; and (v) said proximal region of the reusable shaft having a coupling portion for attachment to a drilling device.

The modular spherical hollow reamer of the present invention solves the problems associated with the prior art reamers. In accordance with the present invention, the modular spherical hollow reamer for medical applications has an easy-to-assemble disposable hollow spherical reamer, which can be attached to a reusable shaft that allows for a fresh reamer to be used with each new application of the reamer. The modular spherical hollow reamer of the present invention transfers shaft torque reliably while at the same time maintains the centerline of the spherical reamer preventing wobbliness thereof during cutting. Bone and bone cement fragments are collected and stored away from the bone cutting area thereby reducing the possibility of bone fragment incorporation into living bone tissue. The modular spherical hollow reamer gradually crates the acetabular bone cavity or resizes an existing acetabular bone cavity, thereby reducing heat during its surgical usage. Owing to the presence of these features, the modular spherical hollow reamer of this invention is safer to use and operates more efficiently than prior art reamers.

The Spherical Hollow Reamer Assembly is adapted to be utilized when preparing bone cavities that receive acetabular cups in a close fitting configuration with precise cavity geometry. The cavities may be prepared from a previously prepared bone cavity in which the acetabular cup has come loose and has to be replaced. In this case, the bone cavity is enlarged and the bone cement previously used has to be completely reamed out and removed. The Spherical Hollow Reamer Assembly may also be used to create a bone cavity on a bone section that has no previously installed acetabular cup. The spherical hollow reamer is disposable, so that the cutting performance of the device is not compromised through repeated use. Several of the clinical problems encountered with conventional reamers are overcome through utilization of the Spherical Hollow Reamers Assembly. Novel design features of the Spherical Hollow Reamer Assembly and improvements to conventional reamers are multifaceted, and include a reusable shaft with a precision threaded distal end adapted to receive a disposable, single-use spherical hollow reamer portion with a corresponding precision threaded central screw providing a center line aligned wobble free attachment of the reamer. The threading on the distal end of the shaft and the mating screw element have counter clockwise thread that do not loosen under the clockwise rotation imparted by the drilling machine. The spherical hollow reamer portion is discarded after a single use to ensure a sharp cutter for use in surgery. Moreover, when dealing with revision acetabular cup surgery, spherical hollow reamers have also been designed to cut bone cement [Polymethylmethacrylate (Acrylic) or PMMA] in a more efficient manner by providing internal space to capture the debris. This reduces both the cutting temperature and time required to remove the remnant cement mantle. Each of these features operates to decrease heat to the bone and reduce operating room time required for acetabular cup revision surgery.

BRIEF DESCRIPTION OF DRAWINGS

The invention will be more fully understood and further advantages will become apparent when reference is had to the following detailed description of the preferred embodiments and the accompanying drawings, in which.

DESCRIPTION OF THE PREFERRED EMBODIMENTS

Figure 1:
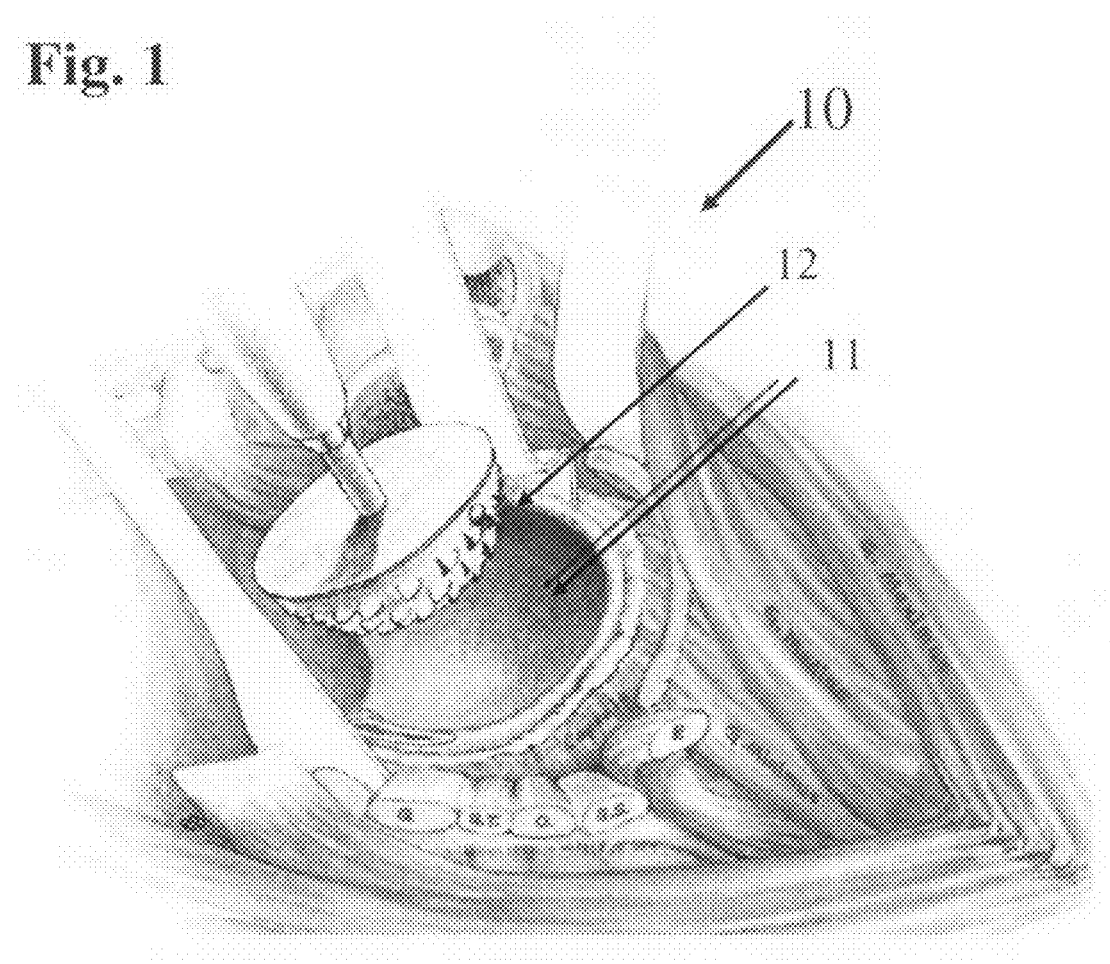
FIG. 1 is a perspective view depicting a medical tapered reamer found in the prior art.

Reaming of bone cavity is required during many orthopedic surgical procedures. These procedures include hip replacement and shoulder replacement and the like. Reaming of the bone cavities for the placement of an acetabular cup requires milling of precisely shaped bone cavity. When the acetabular cup is fixed by interference, this precision is more critical than when the acetabular cup is bonded to the bone cavity by a cement composition. The standard procedure for preparing a bone cavity for acetabular cup insertion is illustrated in FIG. 1 at 10. The bone cavity 11 is milled by a solid reamer 12, which is generally used many times until the teeth of the spherical reamer becomes dull. Due to the presence of debris in the cutting area, the bone surface is subject to over heating and bone tissue degradation. Bone cement fragments may become included into living bone tissue creating bone healing problems.

The invention herein provides spherical hollow reamers appointed for use in medical applications. The spherical hollow reamers are disposable, so that the cutting performance is not compromised through repeated use. Several improvements towards the clinical problems seen with conventional reamers are overcome through utilization of the hollow reamers herein. Novel design features of the hollow reamer herein and improvements to conventional reamers are multifaceted and include a reusable shaft with supporting structure to precisely align a disposable, single-use spherical hollow reamer portion. The hollow reamer portion is discarded after a single use to ensure a sharp cutter for use in surgery. Moreover, when dealing with revision hip surgery, the hollow reamers have also been designed to cut bone cement (PMMA) in a more efficient manner by providing an internal space to capture the bone cement debris and thereby reducing both the cutting temperature and time required to remove the remnant cement mantle. Both these features are important in reducing heat to the bone and reducing operating room time required for revision surgery.

Figure 2:
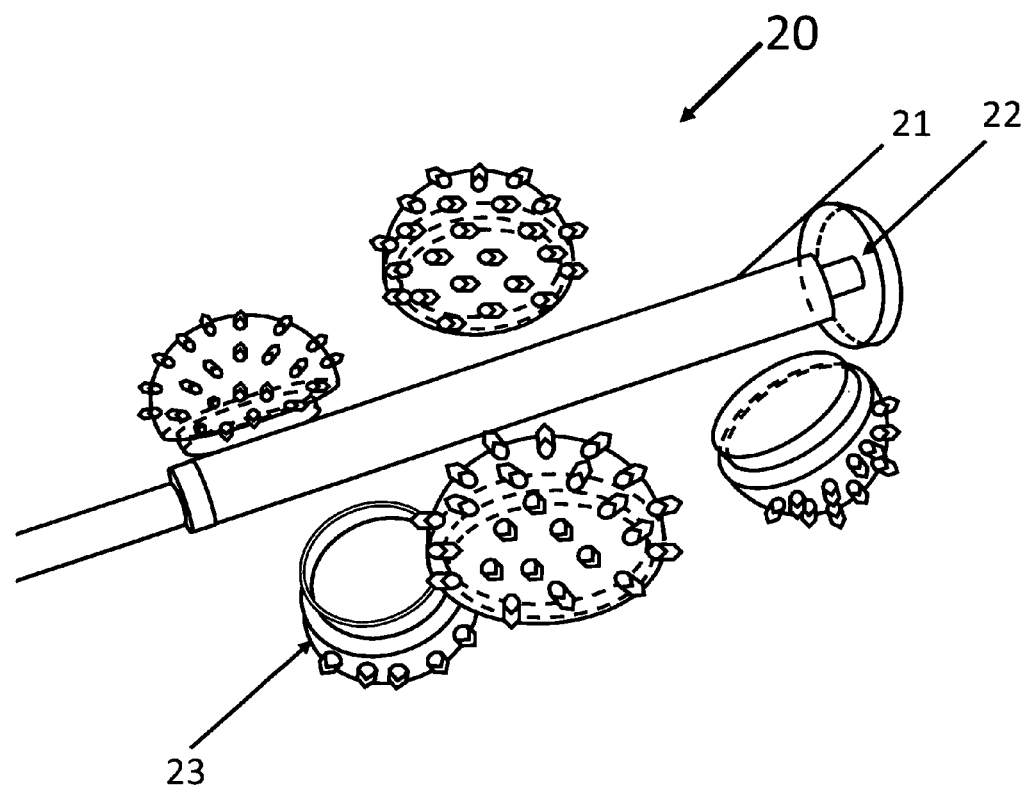
FIG. 2 is a perspective view depicting an easy-to-assemble modular hollow tapered reamer in accordance with the invention.

While FIG. 1 illustrates conventional reamers currently utilized, FIG. 2 illustrates at 20 a photograph the disposable Spherical Hollow Tapered Reamer assembly of the present invention. The spherical hollow reamer assembly comprises at 21 a reusable shaft portion with central plate features 22 and a disposable spherical hollow reamer portion at 23. The central plate 22 shown here is integrally attached to the reusable shaft portion 23.

Figure 3:
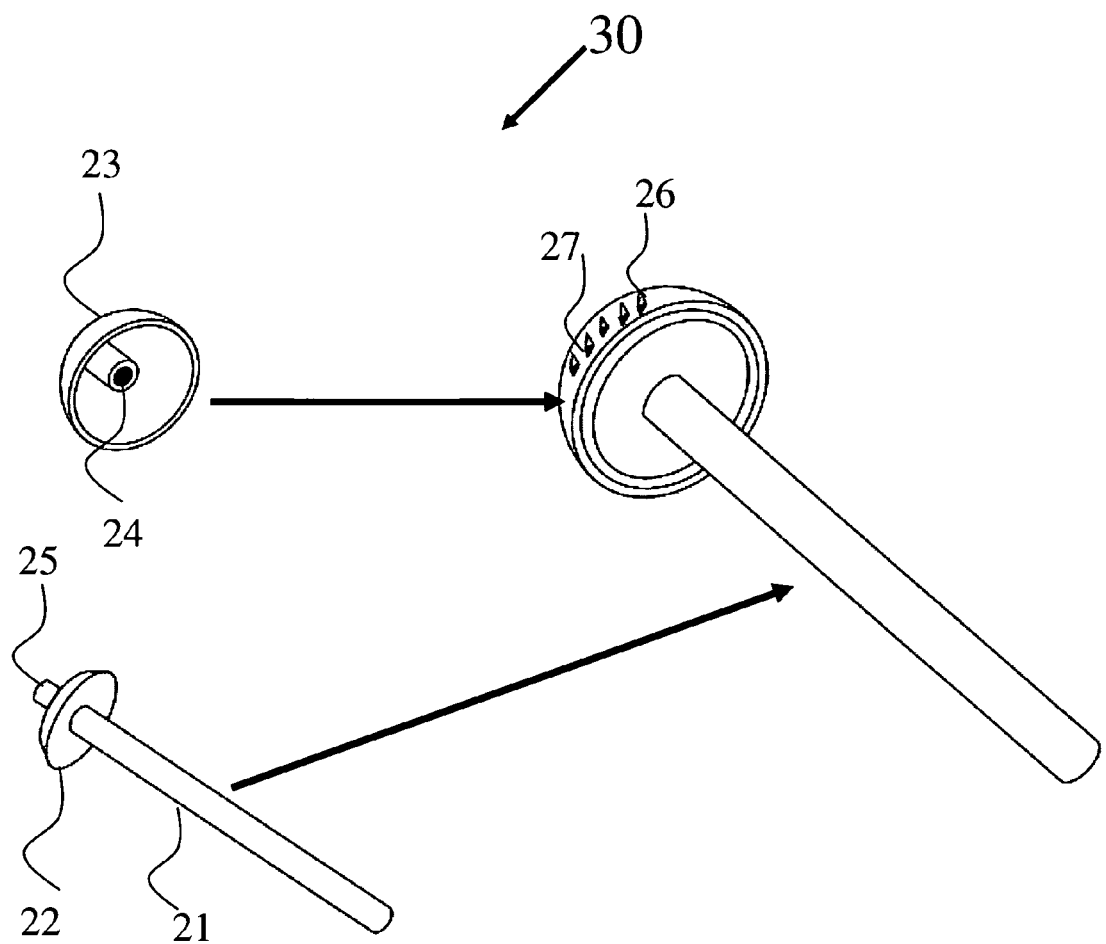
FIG. 3 is a cross sectional view of the easy-to-assemble modular hollow tapered reamer showing mechanical details in accordance with the invention.

FIG. 3 illustrates at 30 the design features of the spherical hollow reamer assembly, wherein a disposable spherical reamer 23 with a precision threaded aperture centrally located 24 engages with a reusable shaft 21 that has a threaded screw 25 at the distal end. The threads are preferably left handed so that right handed rotation of the shaft by the drill during reaming does not loosen the screwed connection between the disposable spherical hollow reamer and the reusable shaft. The spherical hollow reamer 23 has plurality of cutting elements 26 and plurality of apertures 27 that go through the thickness of the disposable hollow reamer 23. A central plate 22 is provided on the shaft, which may be integrally attached to the reusable shaft or attached manually by the user and provides a space for collecting bone fragments or bone cement debris.

FIG. 4A, FIG. 4B and FIG. 4C, illustrates views of the first embodiment of the invention depicting at 40 the modular design of the spherical hollow reamer assembly that provides a reusable reamer shaft and a disposable spherical hollow reamer. The invention includes a reusable shaft 21 that is provided with an integral plate and has a threaded screw at its distal end, which engages with a precision threaded aperture 25 located at the center of the inner surface of the spherical hollow reamer. The plate portion at the central region of the reusable shaft has a taper 28 along its periphery, which engages with the interior surface of the disposable spherical hollow reamer forming a bone fragment and bone cement debris capture volume 29. The disposable spherical reamer is available in the size range from 36 mm to 80 mm in 1 mm size increments. Corresponding shafts are also provided. The disposable spherical hollow reamers have a thickness generally in the range of 0.125 mm to 0.812 mm (0.005" to 0.032").

Figure 4:
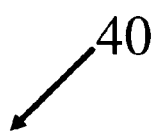
FIG. 4 depicts three views, FIG. 4A, FIG. 4B and FIG. 4C, of the disposable hollow tapered reamer sleeve.
Figure 4:
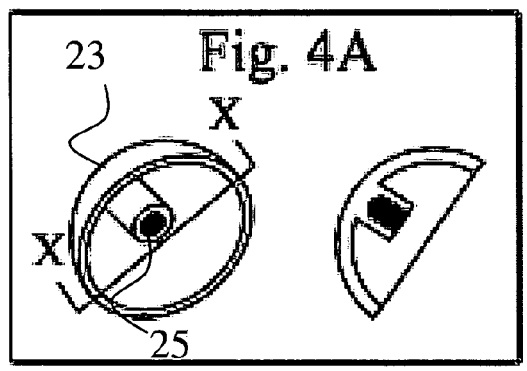
Figure 4:
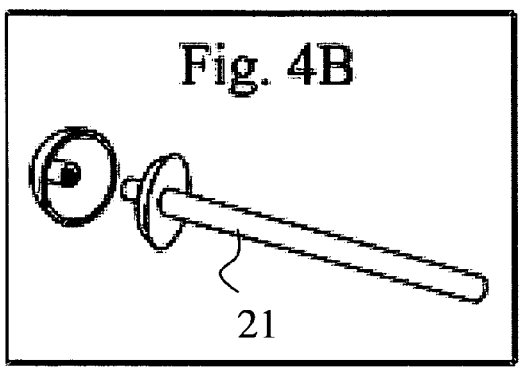
Figure 4:
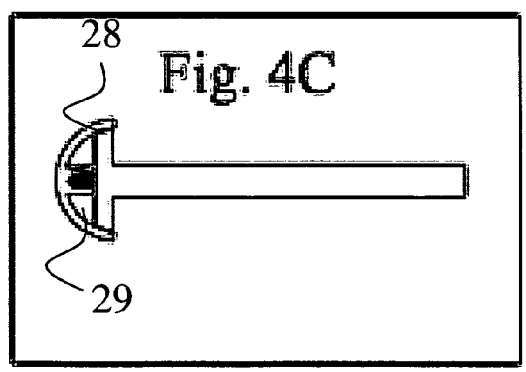
Figure 5:
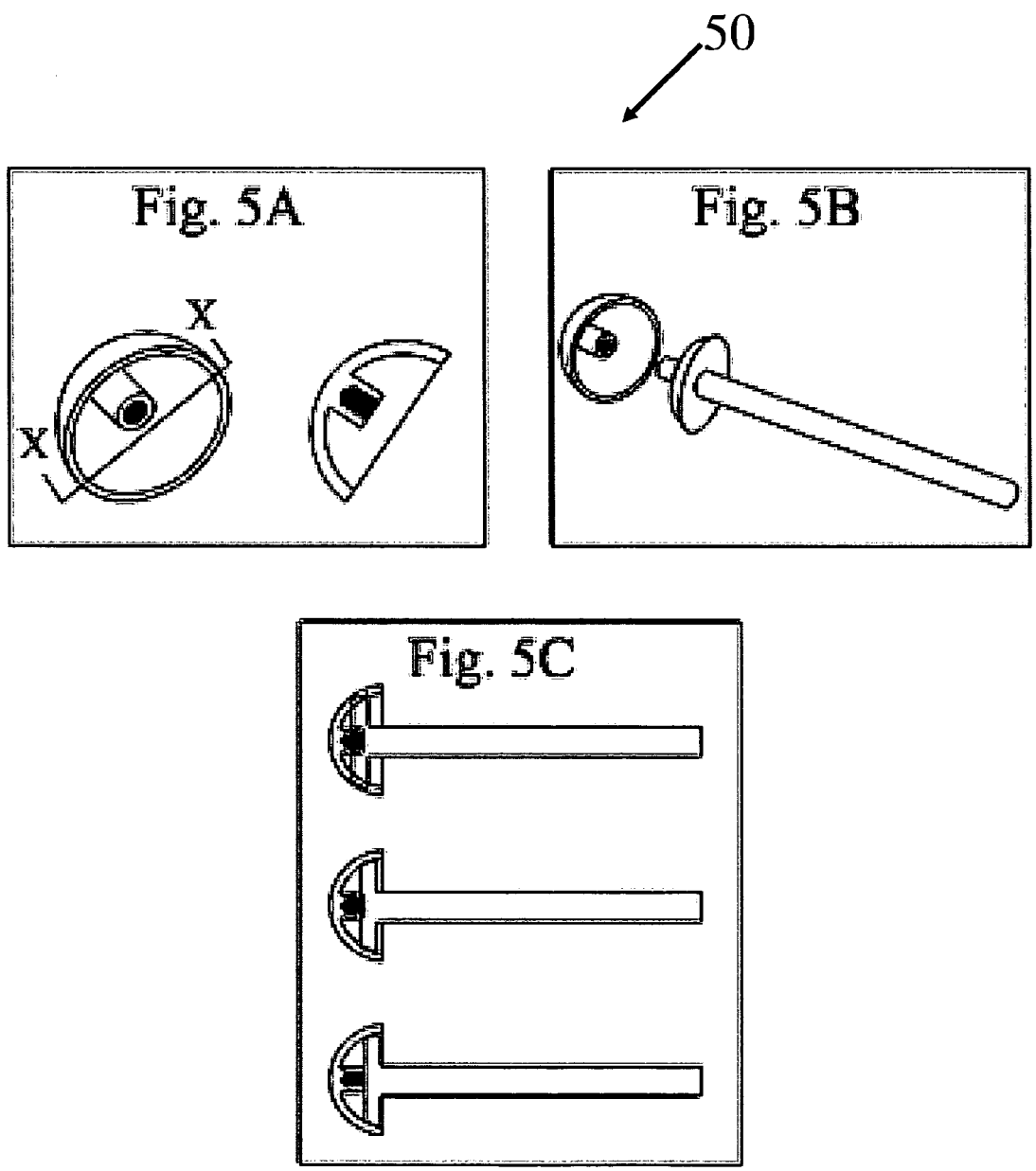
FIG. 5 illustrates a family of disposable tapered hollow sleeves incorporating the elements of the present invention.

FIG. 5 illustrates the second embodiment of the invention depicting at 50 a reusable shaft identical to that shown in FIG. 4, but adapted to engage with three different diameters of disposable spherical hollow reamers. Due to the fixed diameter of the plate provided on the central region of the reusable shaft, the spherical hollow reamer inner surface is engaged at a different location along the axis of the spherical hollow reamer still forming a bone fragment or bone cement debris capturing volume.

Figure 6:
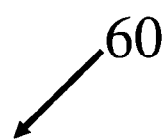
FIG. 6 depicts multiple disposable tapered hollow sleeves attached to a single shaft.
Figure 6:
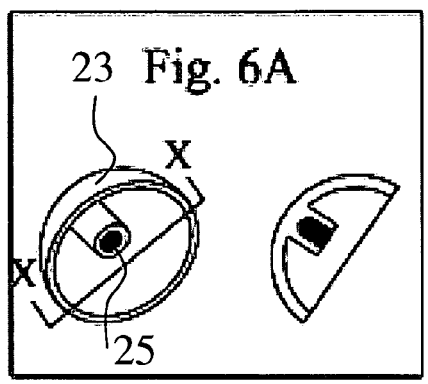
Figure 6:
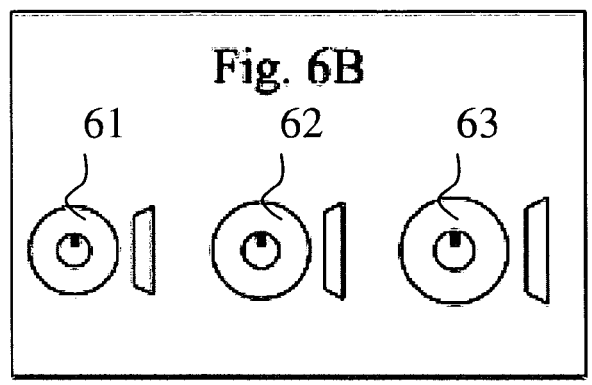
Figure 6:
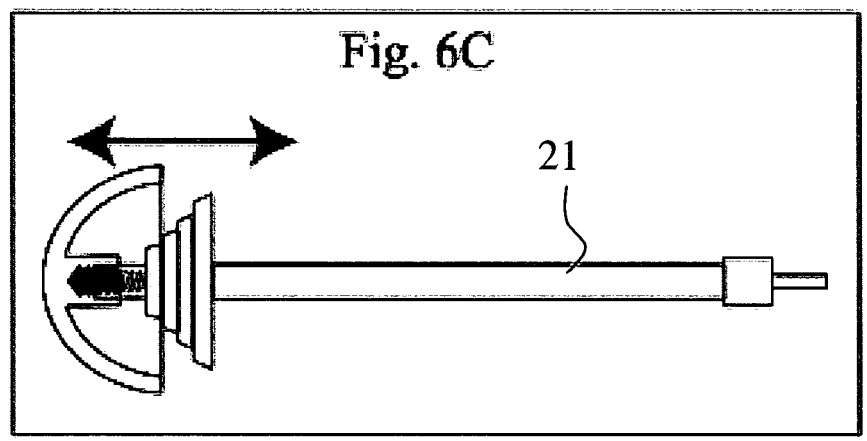

FIG. 6 illustrates at 60 the third embodiment of the invention depicting at 60 a reusable shaft that engages with plurality of user-attached plates 61, 62 and 63 having different dimensions. As the threaded aperture 25 of the central portion of the disposable spherical hollow reamer engages with the reusable shaft 21, of different sizes, it engages with an appropriately sized central plate. This requires the threads to be inserted at different depths as indicated by the arrow shown.

Figure 7:
FIG. 7 provides an assembly view depicting the tapered hollow reamer assembly.
Figure 7:
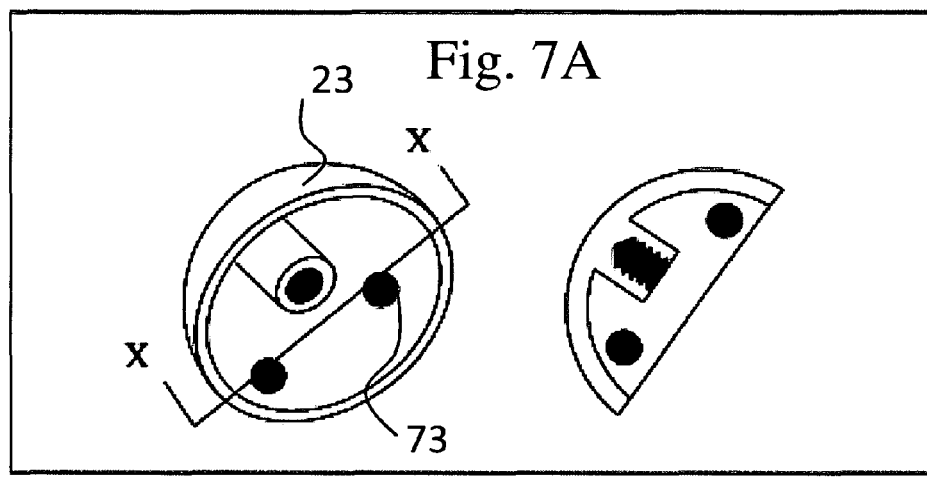
Figure 7:
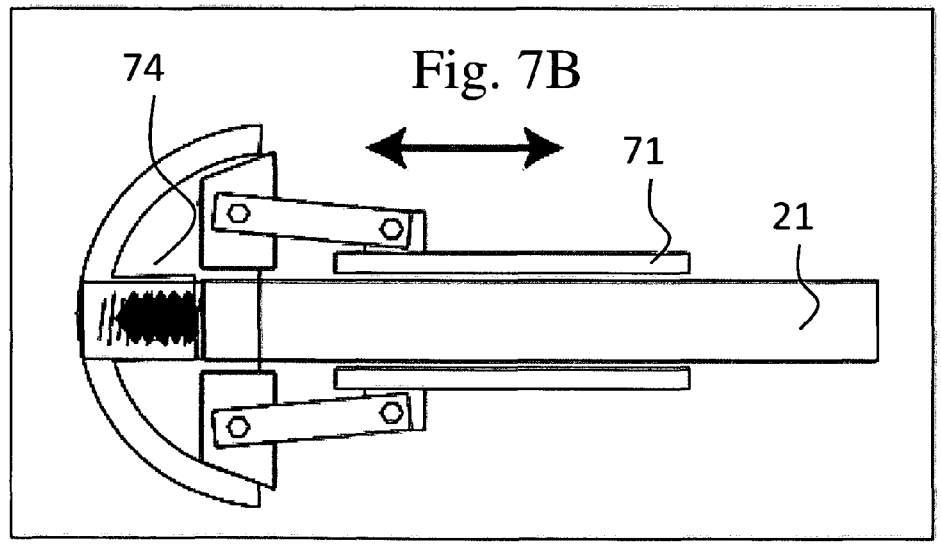

FIG. 7 illustrates at 70 the fourth embodiments of the modular design for the spherical hollow reamer assembly that provides a reusable reamer shaft and a disposable spherical hollow reamer. It includes a single reusable shaft 21 that has an expansion feature 71 that expands in size to fit with all disposable spherical hollow reamers 23, which range from 36 mm to 80 mm with 1 mm size increments. The disposable spherical hollow reamer has holes 73 through the wall of the reamer to inserts screws that engage the expandable portion of the reusable shaft. The distal end of the expandable portion closes the spherical hollow reamer providing a closed space 74 in which bone fragments or bone cement debris accumulates.

Figure 8:
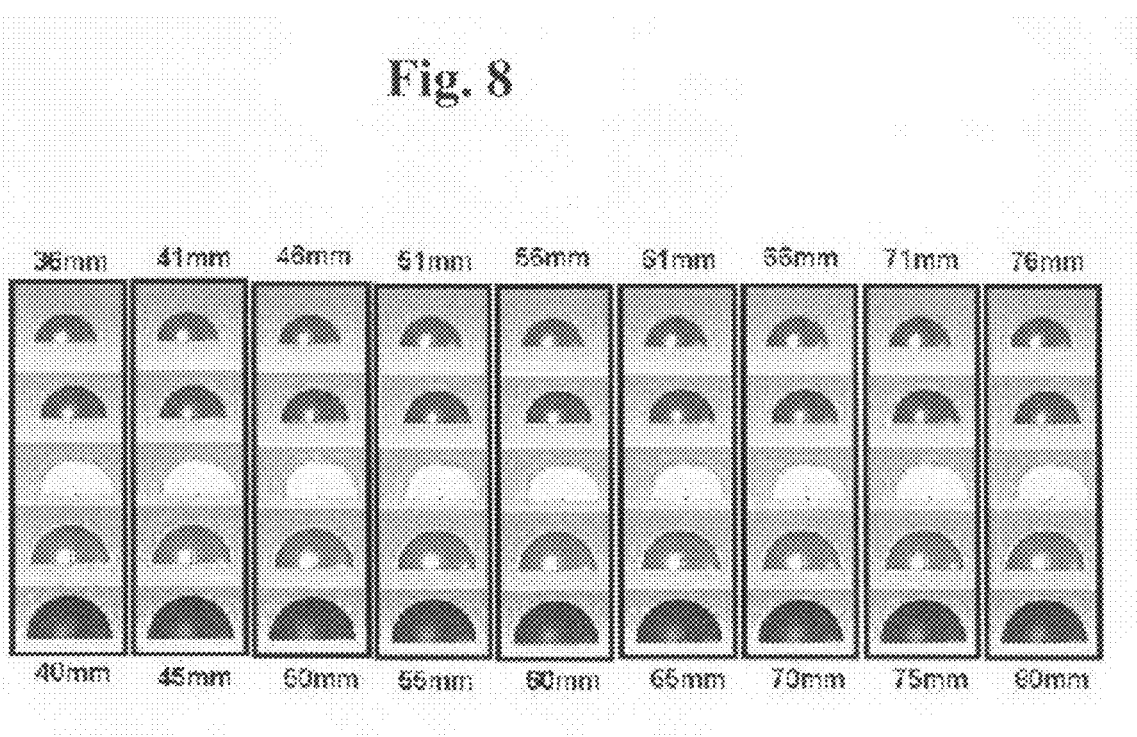
FIG. 8 depicts an alternate embodiment of the tapered hollow reamer assembly.

FIG. 8 illustrates a photograph of family of disposable spherical hollow reamers ranging in diameter from 36 mm to 80 mm in 1 mm increment. The family of disposable reamers addresses a wide range of bone cavity sizes, adapted to fit with corresponding reusable shafts.

In all these embodiments, the disposable spherical hollow reamer portion is provided with plurality of cutting teeth on its outer surface and a plurality of apertures for disposing bone fragments and bone cement fragments away from the reamed area thereby reducing the heat generated at the cutting interface. The spherical hollow reamer is discarded after a single use to ensure a sharp, efficient cutter for every surgery. In each of these different embodiments, the disposable spherical hollow reamer is attached to the reusable shaft using a precisely machined screw thread that engages into a corresponding threaded hole in the distal end of the reusable shaft. The reusable shaft has a plate in the central region that encloses the interior of the spherical hollow reamer creating an enclosed space that captures and retain the bone fragments or bone cement debris that is discharged through the apertures adjacent to the cutters on the outer surface of the spherical hollow reamer. The spherical hollow reamer assembly provides a space for bone debris offering multiple benefits. These benefits include reducing heat generated during cutting by removing the bone debris from the outer surface of the cutter to the inside of the cutter and providing space for bone debris to be collected and later removed for bone grafting for the specific surgical procedure. The space for bone fragment accumulation is in the area between the spherical hollow reamer and the central plate provided on the reusable shaft.

The key features of the spherical hollow assembly for medical applications include, in combination, the components set forth below:

a) a reusable shaft portion having an elongated body with a proximal end, a distal end, and a central plate portion;
b) said proximal end having a coupling portion for attachment of said reusable shaft to a drilling device;
c) said distal end having a precision threaded central screw for receiving a precision threaded screw;
d) said central portion having a conical plate that is user attachable or permanently mounted on the reusable shaft portion; and
e) a disposable spherical hollow reamer portion having an outer surface with a plurality of cutting teeth and a plurality of apertures for discharging bone or bone cement fragments and a an inner surface with a centrally located machined projection with precision threaded aperture;
whereby the screwed attachment of said disposable spherical hollow reamer to the reusable shaft distal end aligns their centerlines preventing wobbliness during reaming, creating precise bone cavities that replicate the shape of the disposable spherical hollow reamer in a medical procedure, and the central portion plate in combination with the spherical hollow reamer forms a containment volume for capturing bone fragment or bone cement fragment.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A disposable hollow acetabular spherical reamer assembly for medical applications, comprising:
   a. a reusable shaft portion having an elongated body with a proximal end, a central conical plate element and a distal end, said proximal end having a coupling portion appointed for attachment of said reamer assembly to a drilling device, said distal end having a male precision threaded portion, and said central conical plate element having a tapered periphery tapering toward said distal end of said reusable shaft portion;
   b. a disposable spherical hollow reamer, comprising:
      1. a hollow construction with an outer surface and an interior surface, said outer surface further comprising a plurality of cutting teeth having a plurality of apertures integrated therein;
      2. said disposable spherical hollow reamer having a centrally located machined projection with a precision threaded aperture; and
      3. said male precision threaded portion of said distal end of said reusable shaft portion being removably screwed into said precision threaded aperture of said centrally located machined projection to drive said reamer;
      4. said tapered periphery of said central conical plate element being received within said interior surface of said disposable spherical hollow reamer so that said central conical plate element sits flush within said interior surface of said disposable spherical hollow reamer;
   c. said central conical plate element contacting the interior surface of the disposable spherical hollow reamer forming an enclosed space with a containment volume for collecting bone fragments and bone cement debris; and
   d. said disposable spherical hollow reamer being assembled onto said reusable shaft portion; whereby a screwed attachment of said disposable spherical hollow reamer to the distal end of said reusable shaft portion aligns their centerlines, preventing wobbliness during reaming and creating precise bone cavities that replicate the shape of the disposable spherical hollow reamer in a medical procedure, and the central conical plate element in combination with the spherical hollow reamer interior surface forms said enclosed space with said containment volume for capturing the bone fragments and bone cement debris and housing same therein during reaming.

2. A reamer assembly for medical applications as recited by claim 1, wherein said disposable spherical hollow reamer has an outer surface diameter in the range of 36 mm to 80 mm.

3. A reamer assembly for medical applications as recited by claim 1, wherein said threaded portion of said distal end of said shaft portion has a left-hand male thread for assembly into said centrally located machined projection of said disposable spherical hollow reamer which has a left handed female thread.

4. A reamer assembly for medical applications as recited by claim 1, wherein said elongated body of said reusable shaft portion further comprises a plurality of graduations to determine a depth of said disposable spherical hollow reamer in a bone cavity during use.

5. A reamer assembly for medical applications as recited by claim 1, wherein said elongated body of said reusable shaft portion further comprises a marking to indicate its size.

6. A reamer assembly for medical applications as recited by claim 1, wherein said disposable spherical hollow reamer further comprises a marking to indicate its size.

7. A reamer assembly for medical applications as recited by claim 1, wherein said reusable shaft portion is solid.

8. A reamer assembly for medical applications as recited by claim 1, wherein said reusable shaft portion is flexible.

* * * * *